United States Patent [19]
Saito et al.

[11] Patent Number: 5,690,852
[45] Date of Patent: Nov. 25, 1997

[54] BABY BOTTLE STERLIZING CONTAINER FOR USE IN MICROWAVE OVEN

[75] Inventors: Hideo Saito, Saitama; Hiroaki Matsuda, Tokyo, both of Japan

[73] Assignee: Combi Corporation, Tokyo, Japan

[21] Appl. No.: 582,616

[22] Filed: Jan. 3, 1996

[30] Foreign Application Priority Data

Jan. 6, 1995 [JP] Japan .................. 7-016460

[51] Int. Cl.$^6$ .................. H05B 6/80; A61L 2/06
[52] U.S. Cl. .................. 219/725; 219/687; 219/762; 219/733; 219/734; 422/21; 422/303; 422/298
[58] Field of Search .................. 219/762, 732, 219/733, 734, 735, 687, 688, 682, 731, 725; 422/21, 303, 300, 302, 297, 298

[56] References Cited

U.S. PATENT DOCUMENTS

| | | | |
|---|---|---|---|
| 4,286,136 | 8/1981 | Mason, Jr. | 219/732 |
| 4,376,096 | 3/1983 | Bowen | 422/307 |
| 4,544,529 | 10/1985 | Hoeck | 422/302 |
| 4,560,455 | 12/1985 | Porta et al. | 204/130 |
| 4,762,973 | 8/1988 | Schultz | 219/756 |
| 4,853,509 | 8/1989 | Murakami | 219/731 |
| 4,978,510 | 12/1990 | Smith | 422/297 |
| 5,213,776 | 5/1993 | Maniero et al. | 422/303 |

FOREIGN PATENT DOCUMENTS

| | | |
|---|---|---|
| 316941 | 2/1991 | Japan . |
| 527937 | 7/1993 | Japan . |

*Primary Examiner*—Philip H. Leung
*Attorney, Agent, or Firm*—Sughrue,Mion,Zinn,Macpeak & Seas PLLC

[57] ABSTRACT

A sterilizing container including a container main body for storing therein a plurality of baby bottles and including an opening for storing therein water used to generate steam when the sterilizing container is inserted into and heated in a microwave oven, a cover member for covering the container main body from the upper portion of the front surface to the upper surface of the container main body and including a water pouring opening in the upper portion of the front surface thereof, a support member stored within the container main body and including a plurality of holders respectively for supporting baby bottles, and a tray member connected to the support member a substantially a right angle and stored within the container main body along the back surface thereof to the bottom surface thereof, the tray member having a certain degree of depth for being able to contain water.

13 Claims, 3 Drawing Sheets

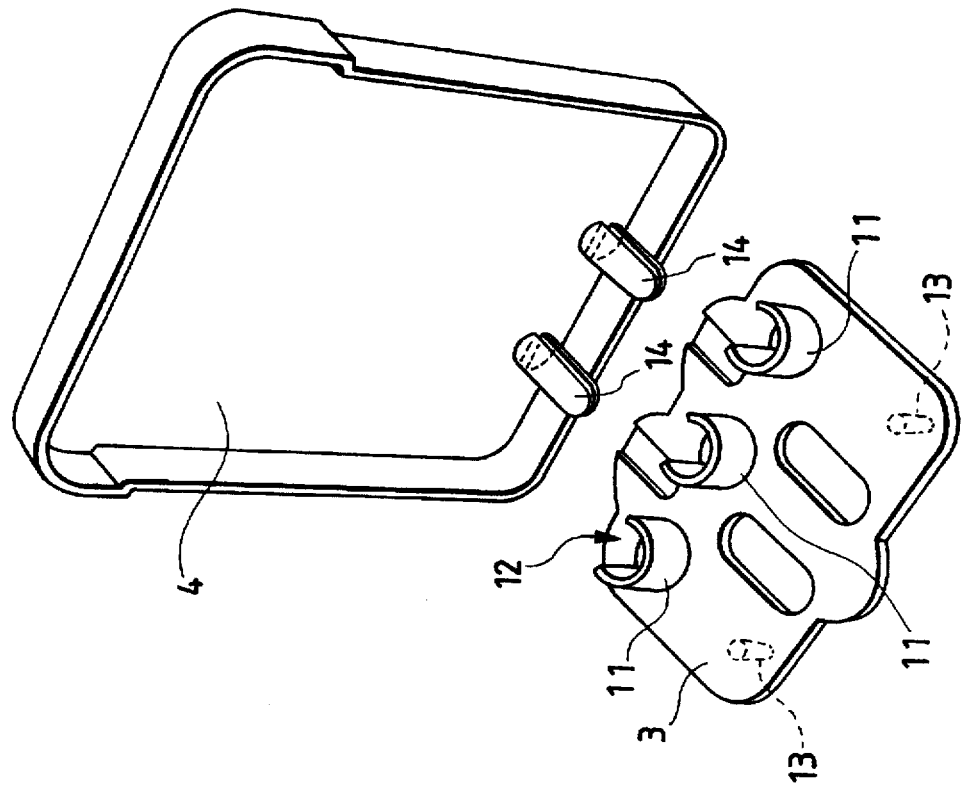
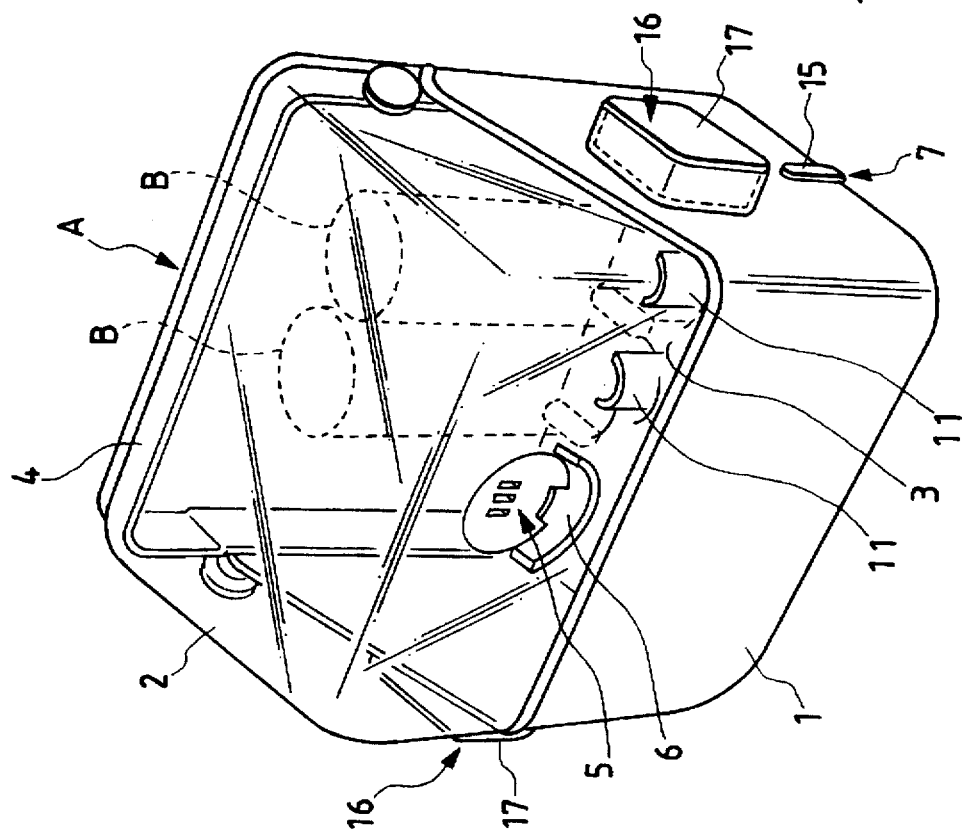

BABY BOTTLE STERLIZING CONTAINER FOR USE IN MICROWAVE OVEN

BACKGROUND OF THE INVENTION

1. Field of the Invention

The present invention relates to a container for storing and sterilizing a plurality of baby bottles therein and, in particular, to a baby bottle sterilizing container for use in a microwave oven which stores water therein and heats and sterilizes the baby bottles by use of a microwave oven.

2. Related Art

When a baby bottle is sterilized in a home, generally, the baby bottle is laid down and dipped in hot water and is then boiled to a certain degree, or the baby bottle is put into a steamer and is exposed to steam for a given period of time. However, in such method, it takes a long time to sterilize the baby bottle and, after sterilized, the baby bottle must be taken out from the hot water or steamer. In this case, it is difficult to take out the baby bottle immediately due the heat of the hot water or steamer and also the sterilized baby bottle must be kept in such a manner that it cannot be contaminated due to the external rubbish, dust or the like. That is, the baby bottle must be handled very carefully.

Accordingly, recently, in order to cope with the above problems, as disclosed in Examined Japanese Utility Model Publication Hei. 5-27937 and in Japanese Utility Model Application No. 1-77692 of Heisei, there have been proposed new methods in which a baby bottle is heated and sterilized by the microwave of a microwave oven using a container which can be inserted into the microwave oven.

The above-mentioned two methods respectively disclosed in Examined Japanese Utility Model Publication Hei. 5-27937 and Japanese Utility Model Application Hei. 1-77692 for sterilizing a baby bottle using a microwave oven are truly desirable in that the bottle can be sterilized in a very short time and the bottle sterilizing operation can also be performed easily. But, in the method disclosed in Examined Japanese Utility Model Publication Hei. 5-27937, since the baby bottle is sterilized only by the microwave of the microwave oven, if the baby bottle, which has been cleaned insufficiently before it is put into the sterilizing container, is sterilized as it is, then the uncleaned portion of the baby bottle will not be removed but rather will be left uncleaned, which is not desirable from the viewpoint of hygiene. Also, since the longitudinal and transverse directions of the sterilizing container are determined and the baby bottle is supported within the sterilizing container in such a manner that it stands up, the height of the sterilizing container must be equal to or greater than that of the baby bottle. Therefore, in some of microwave ovens, there is a possibility that the sterilizing container cannot be inserted into such microwave ovens because the insertion openings thereof are too low in height. Also, some microwave ovens are not structured such that, when the sterilizing container cannot be inserted for the above reason, they cannot be used in such a manner that the sterilizing container is laid down on its side. That is, in the sterilizing method disclosed in Examined Japanese Utility Model Publication Hei. 5-27937, the kinds of microwave ovens are limited and thus this sterilizing method is limited in adaptability. On the other hand, in the sterilizing method disclosed in Japanese Utility Model Application Hei. 1-77692, after water is poured into the sterilizing container, the baby bottle is sterilized by use of a microwave oven, that is, the baby bottle is sterilized by both the microwave of the microwave oven and by steam generated by heating the water. In this method, even if any portion of the baby bottle is left uncleaned, the uncleaned portion can be raised and removed by the steam, thereby being able to eliminate the possibility that the uncleaned portion can be left as it is, as in the before-mentioned sterilizing method. However, since a sufficient amount of water is necessary in order to generate the steam, there is a possibility that the water can be left within the sterilizing container even after completion of the baby bottle sterilizing operation. For this reason, since it is not desirable from the viewpoint of hygiene to leave the sterilized baby bottle as it is, it is necessary to drain the residual water or to transfer the baby bottle to another container. In this case, unless the sterilizing container is conveyed carefully from within the microwave oven to the drain place or to another container, then there is a danger that the residual water can touch the mouth of the baby bottle, which makes it necessary to sterilize the baby bottle again. Also, similarly to the sterilizing method disclosed in the before-mentioned Unexamined Japanese Utility Model Publication Hei. 5-27937, since the longitudinal and transverse directions of the baby bottle are determined and thus the baby bottle must be supported within the sterilizing container in its standing attitude, the height of the sterilizing container must be equal to or greater than that of the baby bottle. And, in order to prevent the residual water from touching the mouth of the baby bottle, a certain degree of clearance is necessary between the mouth of the baby bottle supported within the sterilizing container and the surface of the residual water, which also makes it necessary for the sterilizing container to have a sufficient height. Therefore, in some microwave ovens, such sterilizing container cannot be inserted because the insertion openings of such microwave ovens are too low in height and, in this case, the sterilizing container is not structured such that it can be laid down on its side. This means that the present sterilizing method can use only the limited types of microwave ovens and thus the method is poor in adaptability. Further, if the cover member is not opened carefully, then there is a danger that the water sticking to the inner surface of the cover can drip down onto the baby bottle, which is not desirable from the viewpoint of hygiene.

SUMMARY OF THE INVENTION

The present invention aims at coping with the above-mentioned problems and, accordingly, the object of the invention can be achieved by completing an improved baby bottle sterilizing container to be described below in this specification.

In attaining the above object, according to the invention, there is provided a baby bottle sterilizing container, comprising a container main body for storing a plurality of baby bottles therein and including an opening in the upper portion thereof for storing therein water to be used to generate steam when it is heated by a microwave oven, a cover member for covering integrally the container main body from the upper portion of the front surface of the container main body to the upper surface of the container main body and including a water pouring opening in the upper portion of the front portion thereof, a support member stored within the container main body with a certain degree of height and including a plurality of holders respectively for supporting the baby bottles, and a tray member connected to the support member at substantially a right angle and stored within the container main body along the back surface of the container main body to the bottom surface of the container main body with, the tray member having a certain degree of depth, in which, in the normal position of the sterilizing container, after a sufficient amount of water to generate steam is previously poured into the container main body, or in a case where the insertion opening of the microwave oven is too low for the sterilizing container to be inserted into the microwave oven in the normal position, after water is poured into the tray member stored into the container main body along the back surface of the container main body, if the sterilizing container is inserted into the microwave oven, then the sterilizing container is able to store the water therein and to heat the water by use of the microwave of the microwave oven to thereby sterilize the baby bottle. That is, the present sterilizing container is able to sterilize the baby bottle both in the normal and recumbent position thereof.

Also, in the present baby bottle sterilizing container, a saucer member is provided on the lower side of the water pouring opening formed in the upper portion of the front surface of the cover member, a water drain opening for draining water from the container main body is formed in the bottom surface portion of the container main body, and the cover member is mounted in such a manner that the rear end portion thereof is rotated while it passes the rear side of the back surface of the container main body.

Since the water pouring opening is formed in the upper portion of the front surface of the cover member and the tray member, having a certain degree of depth, is disposed within the container main body along the back surface of the container main body to the bottom surface thereof, in the normal position of the sterilizing container, by previously pouring water from the opening of the container main body in the open state of the cover member, the water can be stored in the lower portion of the container main body and, in the recumbent position of the sterilizing container, by pouring water from the water pouring opening, the water can be stored within the tray member; and, according to the size of the insertion opening of the microwave oven, either of the normal or inverted position direction is selected and the sterilizing container is then inserted into the microwave oven, and heating sterilization by the microwave of the microwave oven and steam sterilization by steam generated by heating the water are used in combination to thereby be able to sterilize the baby bottles efficiently and accurately.

After completion of the sterilization in the normal position of the sterilizing container, the sterilizing container is turned upside down to thereby move the unnecessary water to the tray member stored along the back surface of the container main body to the bottom surface thereof and, after then, the sterilizing container is carried. Also, after completion of the sterilization in the recumbent position of the sterilizing container, the sterilizing container is carried as it is, thereby eliminating the danger that the mouth of the baby bottle can touch the unnecessary water and can be contaminated while the sterilizing container is being carried together with the baby bottle.

Also, since the saucer member is provided on the lower side of the water pouring opening formed in the upper portion of the front surface of the cover member, if water is poured from the water pouring opening in the normal position of the sterilizing container, then the water can be guided by the saucer member and can be poured into and stored in the lower portion of the container main body. Therefore, even if an operator forgets to previously pour water into the container main body, water can be replenished afterwards without opening the cover member.

Further, because the water drain opening for draining water is formed in the bottom surface portion of the container main body, in the normal position of the sterilizing container, by opening the water drain opening while the sterilizing container is held as it is, and, in the recumbent position of the sterilizing container, by standing up the recumbent sterilizing container into its normal position and then by opening the water drain opening, the unnecessary water can be drained easily from the water drain opening and, therefore, there is eliminated the need to open the cover member too many times after completion of the sterilization.

In addition, since the cover member is mounted in such a manner that the rear end portion thereof rotates while it passes the rear side of the back surface of the container main body, if the cover member is opened after completion of the sterilization, then the water sticking to the inner surface of the cover member moves along the surface of the cover member and then drops down externally of the container main body from the back side thereof, thereby being able to eliminate the possibility that the waterdrops can fall down onto the baby bottle or the like.

BRIEF DESCRIPTION OF THE DRAWINGS

FIG. 1 is a perspective view of an embodiment of a sterilizing container according to the invention;

FIG. 2 is an explanatory view to show how to use a sterilizing container according to the invention; in particular, FIG. 2(a) is an explanatory view thereof when it is in the normal position thereof, while

FIG. 3 is a perspective view to explain a support member and a tray member respectively employed in the invention.

DETAILED DESCRIPTION OF THE PREFERRED EMBODIMENTS

Figure 2A:
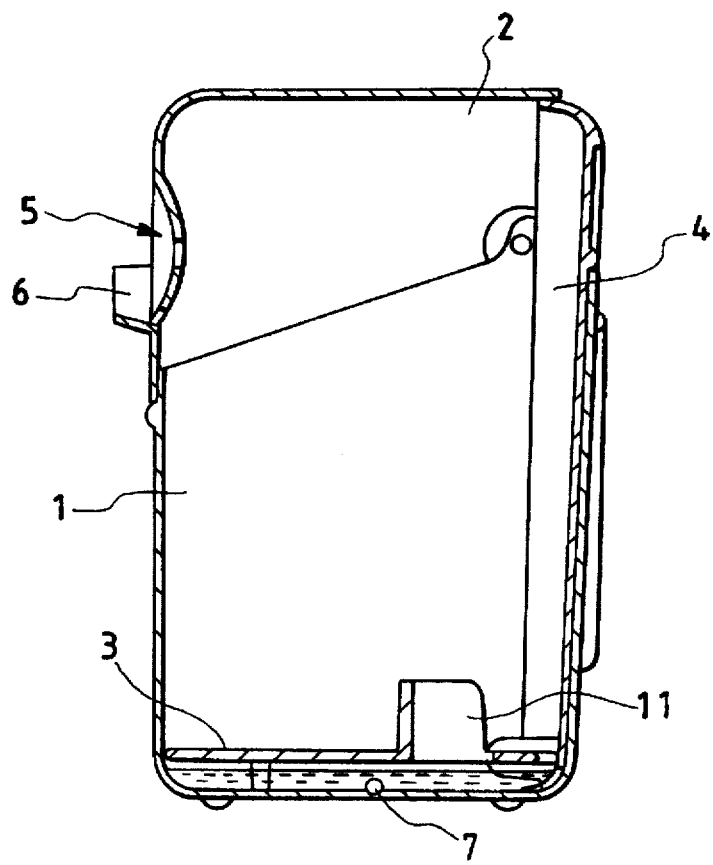
Figure 2B:
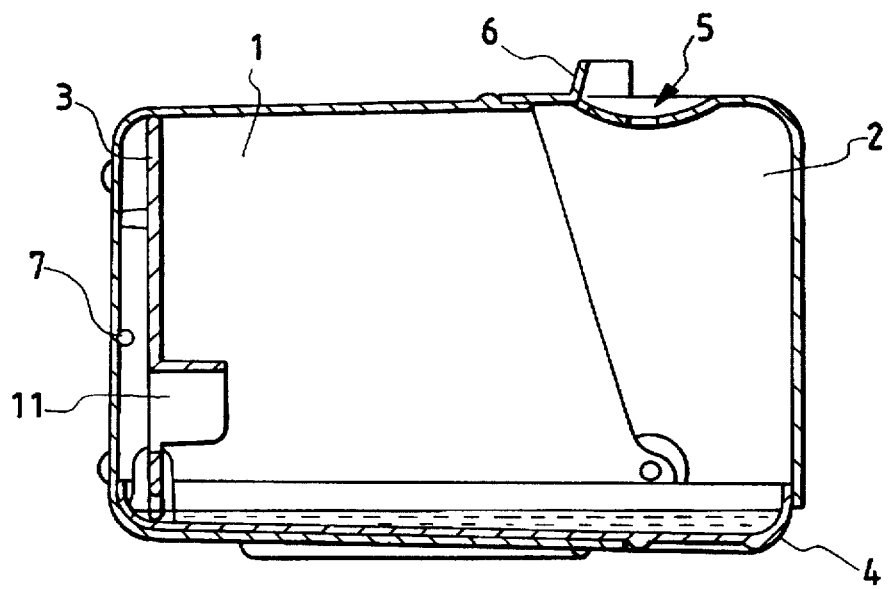
FIG. 2(b) is an explanatory view thereof when it is in the recumbent position.

Now, description will be given below of the embodiments of a baby bottle sterilizing container for use in a microwave oven according to the invention with reference to the accompanying drawings.

The present invention provides a baby bottle sterilizing container (A) for use in a microwave oven, which comprises a container main body (1) for storing therein a plurality of baby bottles (B) and for storing therein water used to generate steam when the sterilizing container (A) is inserted into a microwave oven and is heated therein. The container main body (1) further including an opening formed in the upper portion thereof, a cover member (2) for covering the container main body (1) from the upper portion of the front surface thereof to the upper surface thereof integrally and including a water pouring opening (5) formed in the upper portion of the front surface thereof, a support member (3) stored within the container main body (1) with a certain degree of depth and including a plurality of holders (11) respectively for holding the baby bottles (B), and a tray member (4) connected to the support member (3) substantially at a right angle and stored within the container main body (1) along the back surface of the container main body (1) down to the bottom surface thereof. The tray member (4) has a certain degree of depth. In the present baby bottle sterilizing container (A), the baby bottles are respectively supported in the holders (11) of the support member (3) stored within the container main body (1) and another container (not shown), which includes meshes or slits on the peripheral surface thereof and in which nipples or the like are stored, is stored within the container main body (1)

together with the baby bottles. In the normal position of the sterilizing container, after a sufficient quantity of water to be used to generate steam is previously poured into the lower portion of the container main body (1), the sterilizing container (A) is carried to a position where the microwave oven is situated. On the other hand, when the insertion opening of the microwave oven is too low for the sterilizing container (A) to be inserted into the microwave oven in the normal position, at first, the sterilizing container (A) is carried to the position of the microwave oven and, after then, the sterilizing container (A) is laid down sideways in such a manner that the tray member (4) stored within the sterilizing container (A) along the back surface of the container main body (1) provides the bottom surface of the recumbent sterilizing container (A). Next, a sufficient quantity of water to generate steam is poured into the tray member (4) from a water pouring opening (5) formed in the upper portion of the front surface of the container main body (1) and, after then, the sterilizing container (A) is inserted into and heated in the microwave oven to thereby sterilize the baby bottles. That is, the present sterilizing container (A) is a sterilizing container which can be used both in the normal and recumbent position thereof (see FIGS. 2(a) and (b)).

As described above, in the recumbent position of the sterilizing container, the sterilizing container is not carried to the position of the microwave oven after the water is poured into the tray member (4) previously stored therein along the back surface of the container main body (1). But, the sterilizing container is previously carried to the position of the microwave oven, the cover member (2) is closed, and the sterilizing container is laid down sideways into its recumbent position, before the water is poured into the tray member (4) from the water pouring opening (5) formed in the upper portion of the front surface of the cover member (2). On the other hand, in the normal position of the sterilizing container, since the container main body (1) has a sufficient depth, there is no fear that the water can be choppy and spill out even when the sterilizing container is carried while the water is being stored in the lower portion of the container main body (1). However, in the recumbent position, because the tray member (4) does not have a sufficient depth, if the sterilizing container is carried while the water is being stored therein, then there is some fear that the water can be choppy and spill out and, therefore, the sterilizing container must be carried very carefully, which is troublesome. In other words, the reason why the water is supplied in the last stage after completion of the operation of carrying the sterilizing container in the recumbent position thereof is to eliminate the fear that the water can be choppy and spill out. And, it should be noted here that the present invention provides a structure which can eliminate the above-mentioned fear.

Also, on the two side surfaces of the container main body (1), there are respectively provided grip portions (16, 16) which are used to carry the container main body (1). Each of the grip portions (16, 16) includes a meter (17) which is removably mounted on the grip portion 16 and, when removed, the meter (17) can be used as a container to pour water from the water pouring opening (5) formed in the upper portion of the front surface of the cover member (2).

As the material of the container main body (1), cover member (2), support member (3) and tray member (4), it is preferable to use heat-resistant synthetic resin such as polypropylene, polycarbonate or the like which can stand heating by the microwave of the microwave oven. Also, the cover member (2) may preferably be relatively transparent so that the state of the interior of the sterilizing container can be observed from outside.

Alternatively, according to the invention, there may be formed a water drain opening (7) together with a water drain plug (15) in the bottom surface portion of the container main body (1), so that the unnecessary water can be drained easily after completion of the baby bottle sterilization.

Figure 4:
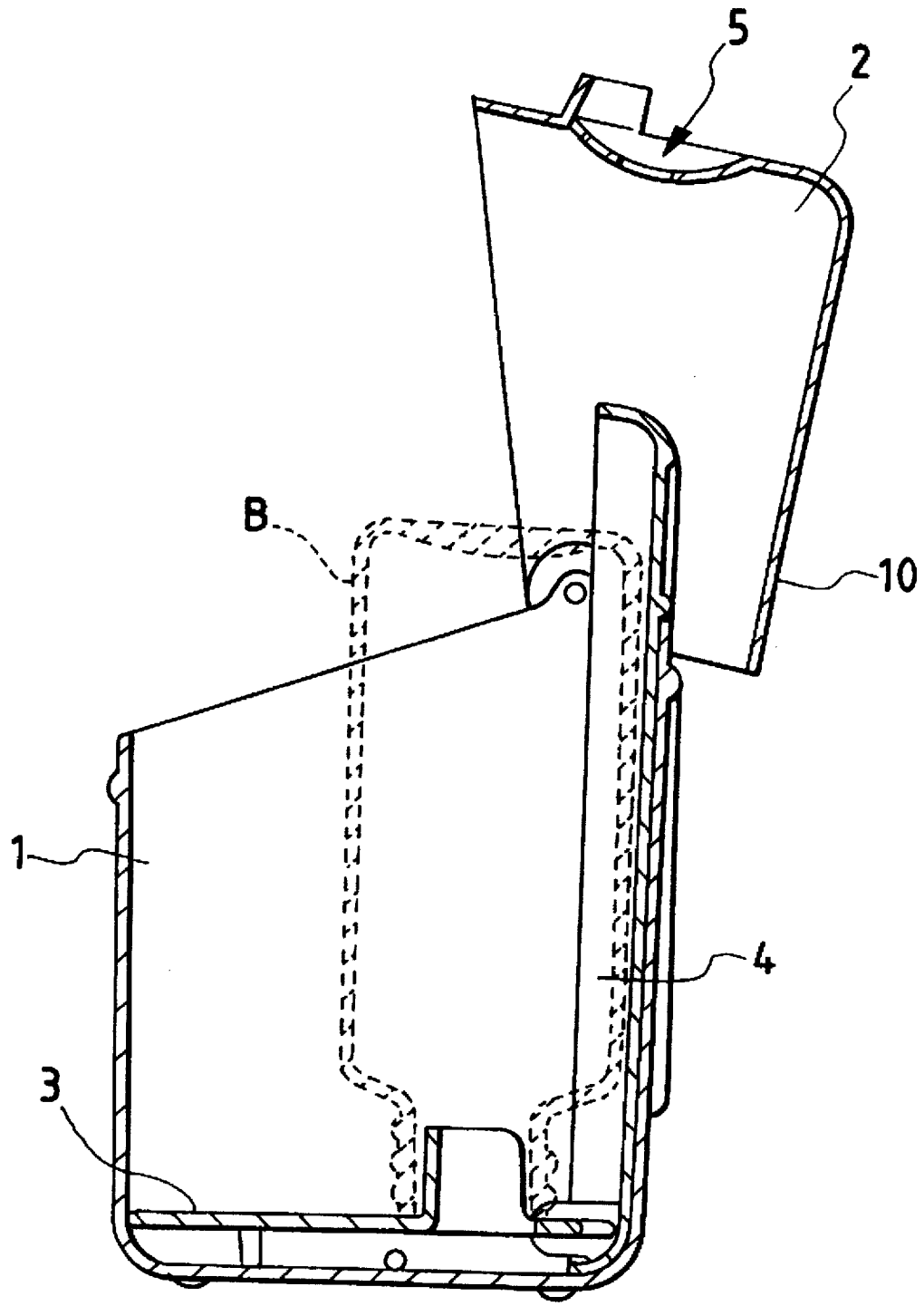
FIG. 4 is an explanatory view of another embodiment of a sterilizing container according to the invention.

The water pouring opening (5) provided in the upper portion of the front surface of the cover member (2) is formed in a slit shape and the periphery of the water pouring opening (5) is generally hollow in order to prevent the water from spilling therefrom. Also, alternatively, there may be formed another slit downwardly of the water pouring opening (5) formed in the upper portion of the front surface of the cover member (2) when the sterilizing container is set in the normal position thereof, and also there may be provided a saucer member (6) in such a manner that the saucer (6) extends along the lower side of the slit, so that water can be supplied into the container main body even when the sterilizing container stands in the normal position thereof. Further, as a still further embodiment of the invention, as shown in FIG. 4, the cover member (2) may be mounted in such a manner that the rear end portion (10) of the cover member (2) can rotate while it passes the rear side of the back surface of the container main body (1), so that the water sticking to the inner surface of the cover member (2) can move along the surface of the cover member (2) and drop down outwardly of the container main body (1) from the back side of the cover member (2), thereby preventing the waterdrops from dripping down onto the baby bottle (B).

Referring now to the support member (3) and tray member (4), as shown in FIG. 3, the support member (3) includes in the surface thereof a plurality of holders (11) respectively fittable with the inner surface of the mouth of each of the baby bottles for supporting the baby bottles, in the back surface thereof a plurality of leg members (13), when the support member (3) is stored within the container main body (1), for supporting the support member (3) with a certain degree of height, and, in the central portion of each of the holders (11), a through opening (12) through which steam can flow in and out and the unnecessary water in the baby bottle can be drained. On the other hand, the tray member (4) is structured such that the peripheral edge portion thereof is generally raised so as to have a sufficient depth to prevent water from spilling away even when the water is poured into the tray member (4), and the tray member (4) includes on the surface thereof two holding members (14) respectively for holding the edges of the support member (3) between them. The support member (3) and tray member (4) are connected together substantially at a right angle. The support member (3) and tray member (4) may also be formed integrally with the container main body (1). However, from the viewpoint of washing, preferably, they may be produced separately and then may be combined together properly.

As has been described heretofore, according to the invention, not only the heating sterilization by the microwave of the microwave oven and the steam sterilization by use of the steam can be used in combination to thereby be able to sterilize the baby bottle within the sterilizing container efficiently and accurately, but also the inserting direction of the sterilizing container into the microwave oven, that is, the normal or recumbent position of the sterilizing container can be properly selected according to the size of the insertion opening of the microwave oven, before it is used to sterilize the baby bottle.

Also, since the frequency of openings of the cover member after completion of the sterilization can be reduced, there can be reduced as much as possible the possibility that trash, dust and the like can get into the sterilizing container through the opened cover member. At the same time, because the unnecessary water can be drained easily by opening the water drain opening for draining water formed in the bottom surface portion of the container main body, the sterilizing container, as it is, can be used as a container for keeping the baby bottle. This eliminates the trouble that, after completion of the baby bottle sterilization, while carefully opening the cover member not to contaminate the baby bottle again, the unnecessary water must drained and the baby bottle must be transferred to another container.

Further, since the present sterilizing container is structured in full consideration that the mouth of the baby bottle can be prevented from being contaminated by the unnecessary water after completion of the baby bottle sterilization as well as the baby bottle can be prevented from being contaminated by the waterdrops when the cover member is opened. That is, the present invention can provide a sterilizing container which is very hygienic.

What is claimed is:

1. A baby bottle sterilizing container for use in a microwave oven, comprising:

a container main body for storing a plurality of baby bottles therein, said container having a front portion, and having a receptacle portion which can hold water;

a cover member for covering said container main body and including a water pouring opening in a front portion of said cover member;

a support member stored within said container main body and including a plurality of holders respectively for supporting baby bottles; and a tray member connected to said support member at a substantially right angle, and stored along a back area of said container main body, said tray member including a receptacle portion which can hold water; wherein in a normal position of the sterilizing container, said tray member is disposed along the back area of said container main body, and in a recumbent position, the sterilizing container is positioned such that said tray member is disposed along a bottom area of said container main body, wherein said sterilizing container is able to store water therein and heat and sterilize baby bottles in a microwave oven in either the normal position or the recumbent position.

2. A baby bottle sterilizing container for use in a microwave oven as set forth in claim 1, wherein said water pouring opening of said cover member includes a saucer member on the lower side of the opening.

3. A baby bottle sterilizing container as claimed in claim 2, wherein said container main body includes a water drain opening for draining water therefrom, said drain opening being disposed towards the bottom of said container main body.

4. A baby bottle sterilizing container as claimed in claim 3, wherein said cover member is rotatably mounted to said container main body in such a manner that, when said cover member is rotated to an open position, a rear end portion of said cover member is positioned relative to said container main body so that water adhering to an inner surface of said cover member can drop outwardly of said container main body, thereby preventing the water from dripping onto a baby bottle disposed in said container main body.

5. A baby bottle sterilizing container as claimed in claim 2, wherein said cover member is mounted in such a manner that, when it is opened the rear end portion thereof is rotated while it passes the rear side of the back surface of said container main body.

6. A baby bottle sterilizing container as claimed in claim 1, wherein said container main body includes a water drain opening for draining water therefrom, said drain opening being disposed towards the bottom of said container main body.

7. A baby bottle sterilizing container as claimed in claim 6, wherein said cover member is mounted in such a manner that, when it is opened the rear end portion thereof is rotated while it passes the rear side of the back surface of said container main body.

8. A baby bottle sterilizing container as claimed in claim 1, wherein said cover member is mounted in such a manner that, when it is opened the rear end portion thereof is rotated while it passes the rear side of the back surface of said container main body.

9. A sterilizing container for use in a microwave oven, comprising:

a container main body including a receptacle portion which can hold water;

a cover connected to said container main body and including a water pouting opening;

a removable support member disposed in said container body, and including at least one holder for holding an item to be sterilized;

a tray member connected to said support member at a substantially right angle, said tray member including a receptacle portion which can hold water; and wherein in a normal sterilizing position of the sterilizing container, said tray member is disposed vertically in a microwave oven, and water poured through said water pouring opening collects in the receptacle portion of said container main body, and wherein in a recumbent sterilizing position, said tray member is disposed horizontally in a microwave oven, and water poured through said water pouring opening collects in the receptacle portion of said tray member, and wherein said sterilizing container is able to sterilize the item to be sterilized when placed in either the normal sterilizing position or in the recumbent sterilizing position.

10. The sterilizing container as claimed in claim 9, wherein the water pouring opening comprises at least one slit in said cover.

11. The sterilizing container as claimed in claim 10, further comprising a saucer portion disposed below the water pouring opening.

12. The sterilizing container as claimed in claim 10, wherein said cover is rotatably connected to said container main body.

13. The sterilizing container as claimed in claim 9, further comprising a water drain plug located towards the bottom of said container main body, and wherein said item to be sterilized is a baby bottle.

* * * * *